United States Patent
Wang et al.

(10) Patent No.: US 10,919,952 B2
(45) Date of Patent: Feb. 16, 2021

(54) METHOD FOR PREPARING COLLAGEN AGGREGATE AND COLLAGEN FROM CHROMIUM-CONTAINING TANNED LEATHER WASTES BY COMBINED ACID-ENZYME CONTROLLED DEGRADATION TECHNOLOGY

(71) Applicants: Xuechuan Wang, Xi'an (CN); Mengdi Hou, Xi'an (CN); Xinhua Liu, Xi'an (CN); Chengyuan Liang, Xi'an (CN); Ouyang Yue, Xi'an (CN); Manhui Zheng, Xi'an (CN); Xing Zhu, Xi'an (CN); Qingxin Han, Xi'an (CN); Ji Li, Xi'an (CN); Huijie Zhang, Xi'an (CN); Taotao Qiang, Xi'an (CN)

(72) Inventors: Xuechuan Wang, Xi'an (CN); Mengdi Hou, Xi'an (CN); Xinhua Liu, Xi'an (CN); Chengyuan Liang, Xi'an (CN); Ouyang Yue, Xi'an (CN); Manhui Zheng, Xi'an (CN); Xing Zhu, Xi'an (CN); Qingxin Han, Xi'an (CN); Ji Li, Xi'an (CN); Huijie Zhang, Xi'an (CN); Taotao Qiang, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 235 days.

(21) Appl. No.: 16/290,859

(22) Filed: Mar. 2, 2019

(65) Prior Publication Data
US 2019/0309051 A1 Oct. 10, 2019

(30) Foreign Application Priority Data
Apr. 9, 2018 (CN) .......................... 201810310443.9

(51) Int. Cl.
*C07K 14/78* (2006.01)

(52) U.S. Cl.
CPC .................................... *C07K 14/78* (2013.01)

(58) Field of Classification Search
CPC ............ C07K 14/78; Y02P 20/54; C12P 21/06
See application file for complete search history.

(56) References Cited

PUBLICATIONS

Jiang, H. et al. The status and developments of leather solid waste treatment: A mini-review, 2016, Waste Management & Research, 399-408 (Year: 2016).*

* cited by examiner

*Primary Examiner* — Louise W Humphrey
*Assistant Examiner* — Anjali Ajit Hirani

(57) ABSTRACT

A method for preparing a collagen from a chromium-containing tanned leather waste is disclosed. The method includes acid dechromation, obtaining a collagen aggregate, and converting the collagen aggregate to the collagen. The method also includes a reaction in a supercritical carbon dioxide reactor.

4 Claims, No Drawings

METHOD FOR PREPARING COLLAGEN AGGREGATE AND COLLAGEN FROM CHROMIUM-CONTAINING TANNED LEATHER WASTES BY COMBINED ACID-ENZYME CONTROLLED DEGRADATION TECHNOLOGY

The present invention claims priority to Chinese Application No. 201810310443.9, filed on Apr. 9, 2018, which is incorporated by reference for all purposes as if fully set forth herein.

FIELD OF THE INVENTION

The present invention relates to the fields of leather chemistry and engineering, more specifically, a method for preparing collagen aggregate and collagen from a chromium-containing tanned leather waste.

BACKGROUND OF THE INVENTION

Chromium-containing tanned leather waste is estimated to be more than 300,000 tons per year in China. The leather industry is subject to more stringent environmental protection regulations. Recycling of chromium-containing tanned leather waste has always been an important research topic in the leather industry, and it is also the only way for the sustainable development of modern leather industry. Extracting collagen from tanned leather waste and processing the collagen into downstream products, such as protein filler, wood adhesive, paper, meet the requirements of green chemistry and sustainable development. In recent years, with the deepening of research on collagen, the application fields of collagen prepared from chromium-containing tanned leather waste have been greatly expanded.

At present, the extraction of collagen from chromium-containing tanned leather waste first requires the dechromation of chromium-containing tanned leather waste. The dechromation includes acid method, alkali method, oxidation method, enzymatic method, etc. The commonly used method is the acid method and alkali method. For the acid method, the dechromation time is long and the dechromation efficiency is low. For the alkali method, the dechromation efficiency is high, but the formed chromium-containing sludge causes secondary pollution and damages the collagen structure. There are many methods for extracting collagen from the waste residue after dechromation, such as, acid method, alkali method, enzymatic method, etc. These methods can be used alone or in combination. A combination of alkali method and enzymatic method has been used in the leather industry, but the alkaline method causes great damage to the collagen structure and only small molecular weight collagen is obtained. Accordingly, the method of extracting collagen from chromium-containing tanned leather waste still has problems, such as, low dechromation efficiency and low molecular weight of the obtained collagen (molecular weight of less than 2000 Dalton).

In view of the above problems of extracting collagen from chromium-containing tanned leather waste, the present invention designs a method includes strong acid treatment, mechanical homogenization, gradient acid method in situ dechromation, weak acid treatment, mechanical dispersion, purification and other means. This method significantly shortens the dechromation time and improves the dechromation efficiency. Finally, the method includes reacting collagen aggregate (as substrate) in a supercritical reactor using supercritical $CO_2$ fluid as reaction medium. Compared with conventional method, the collagen obtained by this method retains the structure and properties of natural collagen and can be used in a variety of applications. The collagen also has larger molecular weight and higher purity, and the extraction yield is also higher.

SUMMARY OF THE INVENTION

In one embodiment, the present invention provides a method for preparing a collagen from a chromium-containing tanned leather waste. The method includes: (1) acid dechromation: immersing the chromium-containing tanned leather waste in a 1.0-5.0 mol/L hydrochloric acid solution for 0.5-3 hours; washing the chromium-containing tanned leather waste with water for 3-5 times to pH=5-7; placing the chromium-containing tanned leather waste in a 0.1-1.0 mol/L oxalic acid solution, the weight of the oxalic acid solution being 20-50 times of the dry weight of the chromium-containing tanned leather waste; transferring the mixture of the chromium-containing tanned leather waste and the oxalic acid solution to a homogenizer; stirring the mixture in the homogenizer at 30-50° C. for 5-48 hours; centrifuging the mixture at a speed of 5000-20000×g and collecting a first precipitate; dispersing the first precipitate in 0.1-1.0 mol/L sodium oxalate solution, the weight of the sodium oxalate solution being 20-50 times of the dry weight of the chromium-containing tanned leather waste; stirring the mixture of the first precipitate and the sodium oxalate solution at 30-50° C. for 24-120 hours; and centrifuging the mixture at a speed of 5000-20000×g and collecting a second precipitate; (2) placing the second precipitate in a 0.1-1.0 mol/L acetic acid-citric acid solution, the weight of the acetic acid-citric acid solution being 20-50 times of the dry weight of the chromium-containing tanned leather waste; transferring the mixture of the second precipitate and the acetic acid-citric acid solution to the homogenizer and stirring the mixture; adding a first 0.1-1.0 mol/L sodium hydroxide solution to the mixture to pH=7.0-7.5; adding 1.0 mol/L ammonium sulfate solution to the mixture and salting out for 10-24 hours; centrifuging the mixture at a speed of 5000-20000×g for 15-30 minutes and collecting a third precipitate; dispersing the third precipitate in a first 0.1-1.0 mol/L acetic acid solution, the weight of the acetic acid solution being 20-50 times of the dry weight of the chromium-containing tanned leather waste; dialyzing in distilled water for 10-48 hours and lyophilizing to obtain a collagen aggregate, and (3) cutting the collagen aggregate; placing the collagen aggregate in a second 0.1-1.0 mol/L acetic acid solution, the weight of the acetic acid solution being 20-50 times of the dry weight of the collagen aggregate; adding a pepsin to the mixture of collagen aggregate and acetic acid solution, the weight of the pepsin being 0.5%-2% of the weight of the collagen aggregate; reacting the mixture in a supercritical carbon dioxide reactor at 40-42° C. and 80-100 atmospheres for 5-24 hours; adding a second 0.1-1.0 mol/L sodium hydroxide solution to the mixture to pH=7.0-7.5; adding a 1.0-1.5 mol/L sodium chloride solution and salting out for 10-24 hours; centrifuging the mixture at a speed of 5000-20000×g for 15-30 minutes and collecting a fourth precipitate; dispersing the fourth precipitate in a 0.1-0.5 mol/L acetic acid solution; dialyzing in distilled water for 10-48 hours and lyophilizing to obtain the collagen.

In another embodiment, the chromium-containing tanned leather waste is a waste from cutting, trimming, or trimming cowhide, sheepskin, or pigskin.

In another embodiment, the acetic acid-citric acid solution in step (2) has a ratio of acetic acid and citric acid of 20:1 to 2:1.

In another embodiment, the reaction in the supercritical carbon dioxide reactor is conducted at 40-42° C. and 80-100 atmospheres for 5-24 hours.

In another embodiment, the collagen is used in wood adhesive, protein filler, paper, and recycled leather.

Compared to conventional methods, the method of present invention has the following advantages:

(1) The method of present invention includes strong acid treatment, mechanical homogenization, gradient acid method in situ dechromation. It significantly shortens the dechromation time and improves the dechromation efficiency.

(2) The collagen aggregate prepared by the method of present invention consists of collagen fibers and collagen fiber bundles, and retains the structure and properties of natural collagen. The collagen has excellent mechanical property, thermal stability, bioactivity, and biodegradability;

(3) The method of present invention includes reacting collagen aggregate in a supercritical fluid reactor, using an acid-enzyme method and in a supercritical $CO_2$ fluid reaction medium. It effectively solved the technical problem that high purity and high extraction rate of collagen could not be achieved simultaneously.

(4) The collagen prepared by the method of the present invention retains the structure and properties of natural collagen, and has larger molecular weight (greater than 10,000 Daltons) that the one prepared by conventional method. The collagen can be used in a variety of applications.

The natural structure of collagen, the molecular weight of collagen is larger than that of the collagen prepared by the prior method (the molecular weight of collagen is more than 10K), the comprehensive performance is more prominent, and the application range is more extensive.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention, example of which is illustrated in the accompanying drawings.

Example 1

(1) acid in situ dechromation: 200 grams of chromium-containing tanned leather waste was immersed in 1.0 mol/L hydrochloric acid solution for 1 hour, and washed with water 5 times to pH=6.7. The chromium-containing tanned leather waste was placed in 5 L of 0.5 mol/L oxalic acid solution. The mixture of the chromium-containing tanned leather waste and the oxalic acid solution was transferred to a homogenizer, and stirred at 40° C. for 48 hours. The mixture was centrifuged at a speed of 5000×g, and a precipitate was collected. The precipitate was dispersed in 5 L of 1.0 mol/L sodium oxalate solution. The mixture of the precipitate and the sodium oxalate solution was stirred at 30° C. for 48 hours, and was centrifuged at a speed of 20000×g and a precipitate was collected.

(2) The precipitate from step (1) was placed in 4 L of 0.2 mol/L acetic acid-citric acid (10:1, molar ratio) solution, and the mixture of the second precipitate and the acetic acid-citric acid solution was transferred to the homogenizer and stirred at a low temperature (e.g., 0° C.). 1.0 mol/L sodium hydroxide solution was added to the mixture to adjust the pH of the mixture to 7.0. 1.0 mol/L ammonium sulfate solution was added to the mixture, and the mixture was salted out for 10 hours. The mixture was centrifuged at a speed of 20000×g for 30 minutes, and a precipitate was collected. The precipitate was dispersed in 4 L of 0.1 mol/L acetic acid solution, dialyzed in distilled water for 10 hours, and lyophilized to obtain a collagen aggregate.

(3) The collagen aggregate from step (2) was cut into pieces, and placed in 2 L of 0.1 mol/L acetic acid solution. Pepsin, 0.5% of the weight of the collagen aggregate, was added to the mixture of collagen aggregate and acetic acid solution. The mixture was then transferred to a supercritical carbon dioxide reactor. Supercritical $CO_2$ fluid was added as reaction medium, and the mixture was reacted at 42° C. and 85 atmospheres for 24 hours. After the reaction is complete, 1.0 mol/L sodium hydroxide solution was added to the mixture to adjust the pH to 7.0. 1.0 mol/L sodium chloride solution was then added to the mixture, and the mixture was salted out for 10 hours. The mixture was centrifuged at a speed of 5000×g for 30 minutes and a precipitate was collected. The precipitate was dispersed in 3 L of 0.5 mol/L acetic acid solution. The steps of adjusting pH, salting out, centrifugation, and dispersion were repeated once. The mixture was dialyzed in distilled water for 48 hours and lyophilized to obtain 76 grams of collagen, a yield of 38%. The range of the molecular weight of the collagen is 11.3K-50.6K Daltons, and medium molecular weight is 35.2K Daltons.

Example 2

(1) acid in situ dechromation: 200 grams of chromium-containing tanned leather waste was immersed in 1.0 mol/L hydrochloric acid solution for 1 hour, and washed with water 5 times to pH=6.7. The chromium-containing tanned leather waste was placed in 5 L of 0.5 mol/L oxalic acid solution. The mixture of the chromium-containing tanned leather waste and the oxalic acid solution was transferred to a homogenizer, and stirred at 40° C. for 48 hours. The mixture was centrifuged at a speed of 10000×g, and a precipitate was collected. The precipitate was dispersed in 5 L of 1.0 mol/L sodium oxalate solution. The mixture of the precipitate and the sodium oxalate solution was stirred at 50° C. for 48 hours, and was centrifuged at a speed of 20000×g and a precipitate was collected.

(2) The precipitate from step (1) was placed in 5 L of 0.5 mol/L acetic acid-citric acid (10:1, molar ratio) solution, and the mixture of the second precipitate and the acetic acid-citric acid solution was transferred to the homogenizer and stirred at a low temperature (e.g., 0° C.). 0.1 mol/L sodium hydroxide solution was added to the mixture to adjust the pH of the mixture to 7.0. 0.5 mol/L ammonium sulfate solution was added to the mixture, and the mixture was salted out for 10 hours. The mixture was centrifuged at a speed of 10000×g for 30 minutes, and a precipitate was collected. The precipitate was dispersed in 5 L of 0.5 mol/L acetic acid solution, dialyzed in distilled water for 10 hours, and lyophilized to obtain a collagen aggregate.

(3) The collagen aggregate from step (2) was cut into pieces, and placed in 3 L of 0.1 mol/L acetic acid solution. Pepsin, 2% of the weight of the collagen aggregate, was added to the mixture of collagen aggregate and acetic acid solution. The mixture was then transferred to a supercritical carbon dioxide reactor. Supercritical $CO_2$ fluid was added as reaction medium, and the mixture was reacted at 40° C. and 80 atmospheres for 12 hours. After the reaction is complete, 0.1 mol/L sodium hydroxide solution was added to the mixture to adjust the pH to 7.0. 1.0 mol/L sodium chloride solution was then added to the mixture, and the mixture was salted out for 10 hours. The mixture was centrifuged at a speed of 5000×g for 30 minutes and a precipitate was collected. The precipitate was dispersed in 3 L of 0.1 mol/L acetic acid solution. The steps of adjusting pH, salting out, centrifugation, and dispersion were repeated once. The mixture was dialyzed in distilled water for 48 hours and lyophilized to obtain 82 grams of collagen, a yield of 41%. The range of the molecular weight of the collagen is 15.7K-40.3K Daltons, and medium molecular weight is 31.7K Daltons.

Example 3

(1) acid in situ dechromation: 200 grams of chromium-containing tanned leather waste was immersed in 1.0 mol/L hydrochloric acid solution for 1 hour, and washed with water 5 times to pH=6.7. The chromium-containing tanned leather waste was placed in 5 L of 0.5 mol/L oxalic acid solution. The mixture of the chromium-containing tanned leather waste and the oxalic acid solution was transferred to a homogenizer, and stirred at 40° C. for 24 hours. The mixture was centrifuged at a speed of 10000×g, and a precipitate was collected. The precipitate was dispersed in 5 L of 1.0 mol/L sodium oxalate solution. The mixture of the precipitate and the sodium oxalate solution was stirred at 50° C. for 24 hours, and was centrifuged at a speed of 20000×g and a precipitate was collected.

(2) The precipitate from step (1) was placed in 5 L of 0.5 mol/L acetic acid-citric acid (10:1, molar ratio) solution, and the mixture of the second precipitate and the acetic acid-citric acid solution was transferred to the homogenizer and stirred at a low temperature (e.g., 0° C.). 0.1 mol/L sodium hydroxide solution was added to the mixture to adjust the pH of the mixture to 7.0. 0.5 mol/L ammonium sulfate solution was added to the mixture, and the mixture was salted out for 10 hours. The mixture was centrifuged at a speed of 10000×g for 30 minutes, and a precipitate was collected. The precipitate was dispersed in 5 L of 0.5 mol/L acetic acid solution, dialyzed in distilled water for 10 hours, and lyophilized to obtain a collagen aggregate.

(3) The collagen aggregate from step (2) was cut into pieces, and placed in 3 L of 0.1 mol/L acetic acid solution. Pepsin, 1.5% of the weight of the collagen aggregate, was added to the mixture of collagen aggregate and acetic acid solution. The mixture was then transferred to a supercritical carbon dioxide reactor. Supercritical $CO_2$ fluid was added as reaction medium, and the mixture was reacted at 41° C. and 90 atmospheres for 12 hours. After the reaction is complete, 0.1 mol/L sodium hydroxide solution was added to the mixture to adjust the pH to 7.0. 1.0 mol/L sodium chloride solution was then added to the mixture, and the mixture was salted out for 10 hours. The mixture was centrifuged at a speed of 5000×g for 30 minutes and a precipitate was collected. The precipitate was dispersed in 3 L of 0.5 mol/L acetic acid solution. The steps of adjusting pH, salting out, centrifugation, and dispersion were repeated once. The mixture was dialyzed in distilled water for 36 hours and lyophilized to obtain 88.8 grams of collagen, a yield of 39.6%. The range of the molecular weight of the collagen is 22.1K-49.0K Daltons, and medium molecular weight is 34.6K Daltons.

Example 4 a. Based on the factors affecting collagen extraction, a single factor experiment was designed. By measuring the chromium content and collagen extraction rate, the optimal time of acid treatment (oxalic acid solution in a homogenizer) in dechromation was determined to be 25 hours. The results are shown in Table 1.

TABLE 1

Collagen Chromium Content and Extraction Rate

| Sample Number | Acid Treatment (hours) | Chromium Content ($mg \cdot L^{-1}$) | Collagen Extraction Rate |
|---|---|---|---|
| 1 | 15 | 0.02130 | 30.86% |
| 2 | 20 | 0.01484 | 32.73% |
| 3 | 23.5 | 0.01990 | 40.21% |
| 4 | 25 | 0.01606 | 44.40% |
| 5 | 29.5 | 0.02173 | 40.15% | b. By optimizing the single factor for the collagen extraction, the optimal process for extracting collagen from chromium-containing tanned leather waste was obtained, including the following steps.

(1) acid in situ dechromation: 200 grams of chromium-containing tanned leather waste was immersed in 1.0 mol/L hydrochloric acid solution for 1 hour, and washed with water 5 times to pH=6.7. The chromium-containing tanned leather waste was placed in 5 L of 0.5 mol/L oxalic acid solution. The mixture of the chromium-containing tanned leather waste and the oxalic acid solution was transferred to a homogenizer, and stirred at 40° C. for 25 hours. The mixture was centrifuged at a speed of 10000×g, and a precipitate was collected. The precipitate was dispersed in 5 L of 1.0 mol/L sodium oxalate solution. The mixture of the precipitate and the sodium oxalate solution was stirred at 50° C. for 24 hours, and was centrifuged at a speed of 20000×g and a precipitate was collected.

(2) The precipitate from step (1) was placed in 5 L of 0.5 mol/L acetic acid-citric acid (20:1, molar ratio) solution, and the mixture of the second precipitate and the acetic acid-citric acid solution was transferred to the homogenizer and stirred at a low temperature (e.g., 0° C.). 0.1 mol/L sodium hydroxide solution was added to the mixture to adjust the pH of the mixture to 7.0. 0.5 mol/L ammonium sulfate solution was added to the mixture, and the mixture was salted out for 10 hours. The mixture was centrifuged at a speed of 10000×g for 30 minutes, and a precipitate was collected. The precipitate was dispersed in 5 L of 0.5 mol/L acetic acid solution, dialyzed in distilled water for 10 hours, and lyophilized to obtain a collagen aggregate.

(3) The collagen aggregate from step (2) was cut into pieces, and placed in 3 L of 0.1 mol/L acetic acid solution. Pepsin, 1.5% of the weight of the collagen aggregate, was added to the mixture of collagen aggregate and acetic acid solution. The mixture was then transferred to a supercritical carbon dioxide reactor. Supercritical $CO_2$ fluid was added as reaction medium, and the mixture was reacted at 41° C. and 90 atmospheres for 12 hours. After the reaction is complete, 0.1 mol/L sodium hydroxide solution was added to the mixture to adjust the pH to 7.0. 1.0 mol/L sodium chloride solution was then added to the mixture, and the mixture was salted out for 10 hours. The mixture was centrifuged at a speed of 5000×g for 30 minutes and a precipitate was collected. The precipitate was dispersed in 3 L of 0.5 mol/L acetic acid solution. The steps of adjusting pH, salting out, centrifugation, and dispersion were repeated once. The mixture was dialyzed in distilled water for 36 hours and lyophilized to obtain 79.1 grams of collagen, a yield of 44.4%. The range of the molecular weight of the collagen is 19.3K-48.8K Daltons, and medium molecular weight is 32.7K Daltons.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for preparing a collagen from a chromium-containing tanned leather waste comprising:
   (1) acid dechromation: immersing the chromium-containing tanned leather waste in a 1.0-5.0 mol/L hydrochloric acid solution for 0.5-3 hours; washing the chromium-containing tanned leather waste with water for 3-5 times to pH=5-7; placing the chromium-containing tanned leather waste in a 0.1-1.0 mol/L oxalic acid solution, the weight of the oxalic acid solution being 20-50 times of the dry weight of the chromium-containing tanned leather waste; transferring the mixture of the chromium-containing tanned leather waste and the oxalic acid solution to a homogenizer; stirring the mixture in the homogenizer at 30-50° C. for 5-48 hours; centrifuging the mixture at a speed of 5000-20000×g and collecting a first precipitate; dispersing the first precipitate in 0.1-1.0 mol/L sodium oxalate solution, the weight of the sodium oxalate solution being 20-50 times of the dry weight of the chromium-containing tanned leather waste; stirring the mixture of the first precipitate and the sodium oxalate solution at 30-50° C. for 24-120 hours; and centrifuging the mixture at a speed of 5000-20000×g and collecting a second precipitate;
   (2) placing the second precipitate in a 0.1-1.0 mol/L acetic acid-citric acid solution, the weight of the acetic acid-citric acid solution being 20-50 times of the dry weight of the chromium-containing tanned leather waste; transferring the mixture of the second precipitate and the acetic acid-citric acid solution to the homogenizer and stirring the mixture; adding a first 0.1-1.0 mol/L sodium hydroxide solution to the mixture to pH=7.0-7.5; adding 1.0 mol/L ammonium sulfate solution to the mixture and salting out for 10-24 hours; centrifuging the mixture at a speed of 5000-20000×g for 15-30 minutes and collecting a third precipitate; dispersing the third precipitate in a first 0.1-1.0 mol/L acetic acid solution, the weight of the acetic acid solution being 20-50 times of the dry weight of the chromium-containing tanned leather waste; dialyzing in distilled water for 10-48 hours and lyophilizing to obtain a collagen aggregate, and
   (3) cutting the collagen aggregate; placing the collagen aggregate in a second 0.1-1.0 mol/L acetic acid solution, the weight of the acetic acid solution being 20-50 times of the dry weight of the collagen aggregate; adding a pepsin to the mixture of collagen aggregate and acetic acid solution, the weight of the pepsin being 0.5%-2% of the weight of the collagen aggregate; reacting the mixture in a supercritical carbon dioxide reactor at 40-42° C. and 80-100 atmospheres for 5-24 hours; adding a second 0.1-1.0 mol/L sodium hydroxide solution to the mixture to pH=7.0-7.5; adding a 1.0-1.5 mol/L sodium chloride solution and salting out for 10-24 hours; centrifuging the mixture at a speed of 5000-20000×g for 15-30 minutes and collecting a fourth precipitate; dispersing the fourth precipitate in a 0.1-0.5 mol/L acetic acid solution; dialyzing in distilled water for 10-48 hours and lyophilizing to obtain the collagen.

2. The method of claim 1, wherein the chromium-containing tanned leather waste is from a cutting or trimming of cowhide, sheepskin, or pigskin.

3. The method of claim 1, wherein the acetic acid-citric acid solution in step (2) has a ratio of acetic acid and citric acid of 2:1 to 20:1.

4. The method of claim 1, wherein the collagen is used in wood adhesive, protein filler, paper, and recycled leather.

* * * * *